(12) United States Patent
Delmi

(10) Patent No.: US 6,607,532 B2
(45) Date of Patent: Aug. 19, 2003

(54) DEVICE FOR PROTECTING SURGICAL PINS

(75) Inventor: Marino Delmi, Vandoeuvres (CH)

(73) Assignee: Newdeal S.A., Vienne (FR)

( * ) Notice: Subject to any disclaimer, the term of this patent is extended or adjusted under 35 U.S.C. 154(b) by 0 days.

(21) Appl. No.: 10/082,126

(22) Filed: Feb. 26, 2002

(65) Prior Publication Data

US 2002/0128656 A1 Sep. 12, 2002

(30) Foreign Application Priority Data

Feb. 26, 2001 (FR) .............................. 01-02577

(51) Int. Cl.[7] .............................................. A61B 17/00
(52) U.S. Cl. ...................................................... 606/72
(58) Field of Search ............................ 606/60, 67, 72, 606/75, 54, 59

(56) References Cited

U.S. PATENT DOCUMENTS

| | | | | |
|---|---|---|---|---|
| 4,628,922 A | * | 12/1986 | Dewar | 606/56 |
| 4,693,240 A | * | 9/1987 | Evans | 606/54 |
| 5,300,072 A | | 4/1994 | Aghion | |
| 5,330,476 A | | 7/1994 | Hiot et al. | |

FOREIGN PATENT DOCUMENTS

| | | |
|---|---|---|
| FR | 2 633 822 | 1/1990 |
| FR | 2 734 470 | 11/1996 |

* cited by examiner

*Primary Examiner*—David O. Reip
*Assistant Examiner*—D. Jacob Davis
(74) *Attorney, Agent, or Firm*—Millen, White, Zelano, Branigan, P.C.

(57) ABSTRACT

A surgical device for holding together and aligning at least two pieces of bone, the device comprising:

a surgical pin suitable for being implanted axially in the pieces of bone to be held together; and a protective plug provided with a through channel for enabling it to be engaged on the pin, said plug including a locking orifice in which locking element can be inserted;

wherein:

the locking orifice is made in such a manner as to open out into the through channel so as to form a surface S; and the locking element presents a matching cross-section such that on being inserted into the locking orifice it can lock the plug relative to the pin.

17 Claims, 2 Drawing Sheets

DEVICE FOR PROTECTING SURGICAL PINS

The present invention relates to the general technical field of surgical pins for holding together and aligning two pieces of bone, in particular finger or toe phalanges, the two pieces of bone being held together by being put into contact with each other.

The present invention provides a surgical device for holding together and aligning at least two pieces of bone, the device comprising:

- a surgical pin suitable for being implanted axially in the pieces of bone to be held together; and
- a protective plug provided with a through channel for enabling it to be engaged on the pin, said plug including a locking orifice in which locking means can be inserted to lock the plug in position relative to the pin.

BACKGROUND OF THE INVENTION

In various surgical situations, for example with bone deformations or fractures in the phalanges of the foot or the hand, it is necessary to cause the phalanges of the foot or the hand to be held together.

In general, surgeons then make use of external mechanical elements designed, over a determined length of time, to hold together and keep in place bone fractions so as to allow osteosynthesis to take place.

Thus, it is already known that use can be made of compression clips. However they are not in general use and they suffer from various drawbacks associated in particular with the pieces of bone for holding together often not being held sufficiently stably. Compression clips also suffer from a drawback associated with the difficulty of putting them in place, with it often being extremely difficult to find a particular axial direction and then to maintain it.

That is why it is often preferred to use techniques that involve inserting a surgical pin through the skin, with the pin being engaged axially through the pieces of bone that are to be held together.

Recourse to metal pins passing through all or part of two pieces of bone to be held together naturally presents the advantage of enabling the pieces of bone to be held on an axial direction that is particularly well aligned. In general, such a pin is put into place with the help of a motor to facilitate causing the free end of the pin to penetrate into the bone, while the non-penetrating free end is then necessarily present at the percutaneous level of the foot or the hand. This free end can present a certain amount of danger and consequently it is generally curved by the surgeon.

In order to reduce the risk of catching or injury, metal or plastic protection pieces also exist that form a kind of plug which is threaded onto the pin from the free end via a through channel formed in the mass of the plug.

Presently-known devices of that type comprise a spherical protective plug pierced along an axis of symmetry by a channel of cylindrical section. Such a known device is also provided with a tapped locking orifice opening out into the through channel and extending along a direction that is substantially orthogonal thereto. The locking orifice contains a grub screw that can be moved to constitute means for locking the plug and the pin in some relative position. Once the pin is in place and the plug has been engaged using its through channel, the plug can be locked in position by the lock screw, which, on being tightened, presses against the pin where the through channel intersects the locking orifice.

Consequently, that device provides a degree of protection for the free end of the pin and avoids the patient being injured or catching on various obstacles in the course of daily life. Once bone fusion has been achieved, the surgeon then removes the pin making use of pliers that enable the pin to be twisted and extracted axially so that it can slide. Although presently-known devices make a positive contribution to protecting the end of the pin, they are relatively ineffective when it comes to the handling required for extracting the pin, which means that it is necessary to make use of an additional tool for providing assistance in extraction.

Such a known device naturally provides a positive contribution to protecting patients, but it nevertheless suffers from various drawbacks, and in particular the need to use an inside thread in the locking orifice. This is difficult to provide on elements that are as small as the protective plugs used, so the threading operation is difficult to achieve industrially. Furthermore, such an operation gives rise to non-negligible additional expense, particularly since such an operation can be performed only by using high precision equipment that is correspondingly expensive.

Furthermore, making such a device turns out to give rise to additional problems with unmolding of the parts and that has led to the use of such known devices being somewhat limited.

OBJECTS AND SUMMARY OF THE INVENTION

Consequently, the objects given to the invention lie in finding a remedy to the various drawbacks mentioned above and in proposing a novel surgical device for holding pieces of bone together and aligning them, and in particular for the phalanges of the foot or the hand, such a device being particularly simple to make and to use, and in particular being easy to extract, while nevertheless being low in cost.

Another object of the invention seeks to propose a novel surgical device that reduces the risks of catching or of injury to the patient.

Another object of the invention seeks to propose a novel surgical device making it particularly simple and reliable to lock a protective plug into place on a surgical pin.

Another object of the invention seeks to propose a novel surgical device enabling a common size of plug to be fitted to surgical pins of various diameters.

Upon further study of the specification and appended claims, further objects and advantages of this invention will become apparent to those skilled into the art.

These objects of the invention are achieved by means of a surgical device for holding together and aligning at least two pieces of bone, the device comprising:

- a surgical pin suitable for being implanted axially in the pieces of bone to be held together; and
- a protective plug provided with a through channel for enabling it to be engaged on the pin, said plug including a locking orifice in which locking means can be inserted to lock the plug in position relative to the pin;

wherein:

- the locking orifice is made in such a manner as to open out substantially tangentially into the through channel so as to form a surface S; and
- the locking means presents a matching cross-section such that on being inserted into the locking orifice it can lock the plug relative to the pin by compressive/locking contact via the surface S.

BRIEF DESCRIPTION OF THE DRAWINGS

The invention will be better understood on reading the following description and the accompanying drawings, which are provided purely for non-limiting explanatory purposes, and in which.

MORE DETAILED DESCRIPTION

Figure 1:
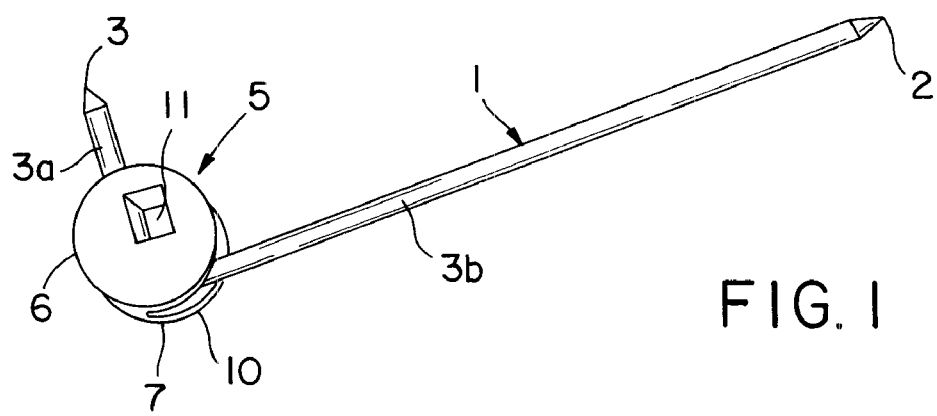
FIG. 1 is a perspective view of a surgical device in accordance with the invention and comprising a surgical pin and a protective plug prior to engaging the locking means.

The surgical device shown in FIGS. 1 to 8 is intended to hold together and align at least two pieces of bone (not shown in the figures) so as to encourage osteosynthesis. In the description below, particular reference is made to holding together bones in the phalanges of the foot or the hand, it being understood that the surgical device of the invention is not limited in any way to holding together bones of that type, and that such an application is merely a preferred application.

The surgical device of the invention comprises a surgical pin 1 suitable for being implanted axially in the pieces of bone that are to be joined together. For this purpose, the surgical pin 1 is in the form of a rod presenting good mechanical strength, for example being made out of a metal that is suitable for medical use. The surgical pin 1 is generally in the form of a tapering cylinder, having a thickness of a few millimeters and it is a few centimeters long, being provided at both ends 2 and 3 with a chamfer or sharp tip for making it easier to pierce or penetrate into the bones that are to be joined together. Prior to use, the surgical pin is rectilinear, but it is of mechanical strength that is suitable for allowing a surgeon to bend it easily without breaking it. The surgical pin 1 is, for example, made of metal, such as stainless steel or titanium.

The surgical device of the invention also has a protective plug 5, e.g. made of a plastics material suitable for medical use, for example generally in the shape of a substantially cylindrical body of revolution defining two opposite faces 6 and 7 that are substantially plane and united by a cylindrical envelope 8. Preferably, the protective plug is made of injectable plastic material such as polycarbonate or polypropylene. The protective plug 5 has a through channel 9 passing through the mass of the body of the protective plug 5 so as to form a rectilinear channel extending between two points of the cylindrical envelope 8. The through channel 9 is advantageously of constant diameter, e.g. a diameter that is perceptibly greater than the diameters usually used for conventional surgical pins, so as to make it easy to pass the surgical pin 1 through said through channel 9.

In a preferred version of the invention, as shown in FIGS. 1 to 3 and 7, the surgical pin 1 is intended to be bent by the surgeon while it is being implanted, so it is particularly advantageous for the protective plug 5 also to have a guide slot 10 for the surgical pin 1 passing through the mass of the plug 5 and the cylindrical envelope 8.

Figure 7:
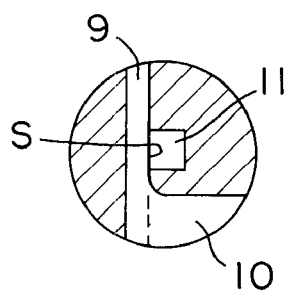
FIG. 7 is a cross-section view identical to that of FIG. 6 showing a detail of a preferred variant of the body of the locking means.

As shown in FIG. 7, the guide slot 10 extends from the through channel 9 and opens out therein (or vice versa), preferably in a direction that is perpendicular thereto so as to form a bend of about 90°. The guide slot 10 extends as far as the cylindrical envelope 8 where it opens out, forming a U-shape with two side flanks enabling the surgical pin 1 to be guided and locked between them.

Figure 2:
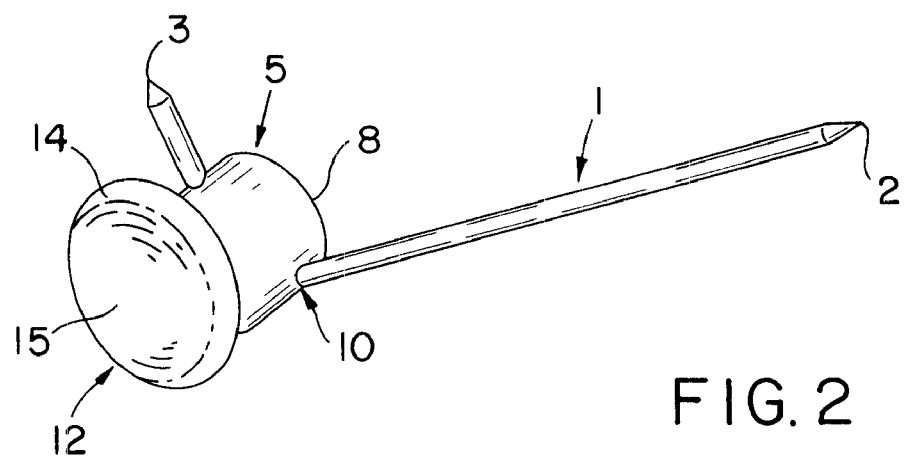
FIG. 2 is a perspective view corresponding to FIG. 1 showing a surgical device of the invention together with locking means prior to breaking off its head.
Figure 3:
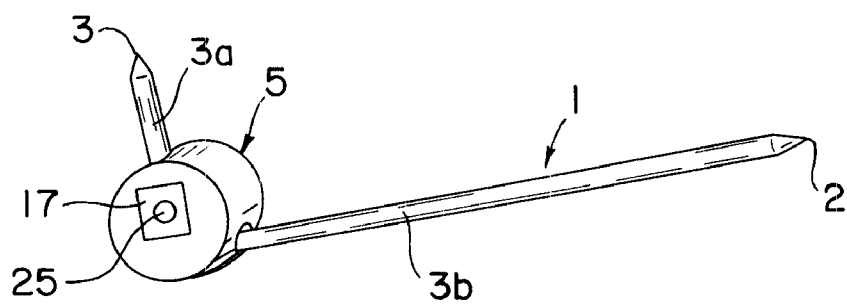
FIG. 3 is a view analogous to FIGS. 1 and 2 showing a surgical device of the invention after the head of the locking means has been broken off.

As shown in FIGS. 1 to 3, the through channel 9 extends along the direction represented by the branch 3a of the surgical pin 1, while the guide slot 10 extends substantially perpendicularly to the branch 3a within a fraction of the cylindrical envelope 8 and in the direction of the branch 3b at the outlet from the through channel 9.

The protective plug 5 also has a locking orifice 11 that is preferably a through orifice, formed in the mass of the cylindrical body 8 between the two faces 6 and 7, and in which a locking means 12 is designed to be inserted so as to lock the relative position between the protective plug 5 and the surgical pin 1.

In accordance with the invention, the locking orifice 11 is made in such a manner as to open out substantially tangentially into the through channel 9 so as to form a common opening or interface S, the locking means 12 being of matching cross-section so that when it is inserted into the locking orifice 11 it can lock the protective plug 5 relative to the surgical pin 1 by compressive/locking contact at and via said surface S. The locking orifice 11 opens to the side and over a fraction of the length of the through channel 9 allowing the locking means 12 to compress the branch 3a of the surgical pin 1 against a portion of the surface of the through channel 9, thereby locking it in place and preventing it from moving in translation.

By means of these characteristics, the plug 5 is thus locked axially on the pin 1, thus making it possible for the plug 5 to be used effectively as handle means for subsequently extracting the pin 1 axially. When the plug 5 is also provided with a guide slot 10 for bending the pin 1, the combination of bending and axial locking reinforces the stability of the plug 5 in rotation. This feature makes it much easier to extract the pin 1 since in all directions in which it can be handled from the outside (combined axial and rotary actions), the plug 5 remains stable and secured to the pin 1.

As shown in FIGS. 1 to 7, the locking orifice 11 is made so as to extend in a direction that is substantially orthogonal to the through channel 9. Advantageously, its cross-section is substantially constant in shape and is of dimensions that match those of the locking means 12. The cross-section of the locking orifice 11 can advantageously be substantially in the form of a parallelogram, e.g. a rectangle or a square, but the section could also be circular, oval, or arbitrary.

In the invention, the locking means 12 is advantageously implemented in the form of a pusher 17 having a push head 14 forming a cup with a push face 15 that is advantageously concave. Projecting from the face 16 opposite to the push face 15, there extends the pusher element 17 proper which is designed to be inserted in the locking orifice 11.

In the invention, the pusher element 17 is of cross-section and of dimensions that match and are complementary in shape to the cross-section of the locking orifice 11, the cross-section of the pusher element 17 increasing, preferably smoothly, from its insertion end 18 towards the face 16.

Figure 4:
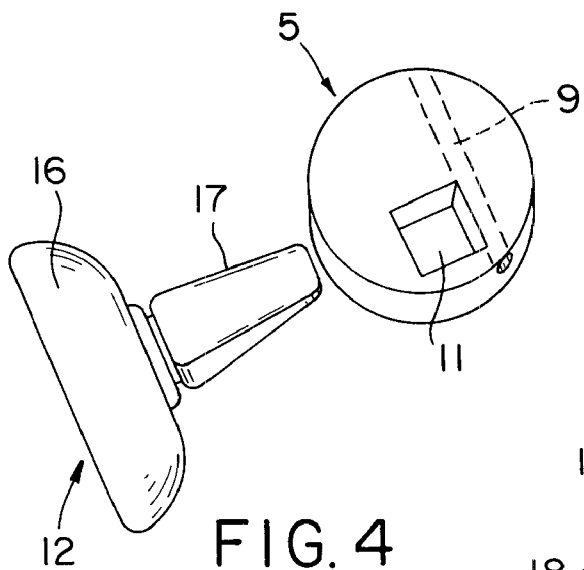
FIG. 4 is a side view in perspective showing a detail of the locking means and of the protective plug.
Figure 5:
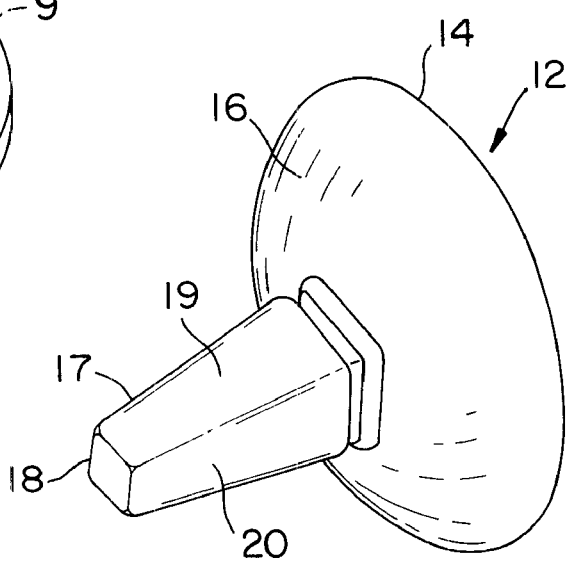
FIG. 5 is a perspective view showing a detail of the locking means before it is broken.
Figure 6:
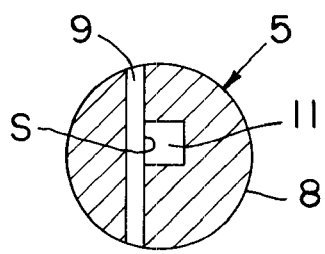
FIG. 6 is a cross-section view showing a detail of the body of the locking means.

As shown in FIGS. 4 and 5 in particular, the cross-section of the locking orifice 11 is in the form of a parallelogram, e.g. a square or advantageously a rectangle, with the cross-section of the pusher element 17 likewise being in the form of a parallelogram, and respectively square or rectangular, while also being generally tapering, as shown. Advantageously, the rectangular section of the pusher element 17 thus extends along a sloping generator line.

Figure 8:
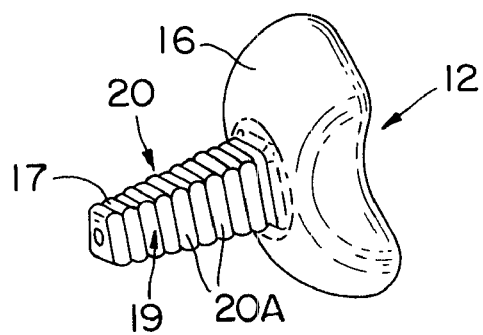
FIG. 8 is a perspective view showing a preferred embodiment.

In a particularly advantageous version of the invention, the pusher element 17 has a cross-section that is rectangular, extending along a sloping generator line as shown in FIGS. 4, 5, and 8, serving to define a wider section and a narrower section, respectively revealed by two wider faces 19 and two narrower faces 20.

This feature makes it possible to select the orientation of the pusher element 17 on insertion as a function of diameter of the surgical pin 1 used. Thus, if the surgical pin 1 used is of large diameter then the pusher element 17 should be oriented in the locking orifice 11 so as to present its smaller section so that one of its broader faces comes into compressive contact against the surgical pin 1 via the surface S.

Conversely, if the pin used is of smaller diameter, then on the contrary it is necessary to present the larger section so that one of its narrower faces comes into compressive contact via the surface S with the smaller diameter surgical pin 1.

In the embodiments shown in FIGS. 4 and 5, the surfaces of the faces 19 and 20 are plane. In a preferred variant (FIG. 8) the faces 19 and 20 can be provided with portions in relief, for example transversely-extending catches 20A that encourage jamming and prevent the element from being extracted from the locking orifice 11.

In practice, the diameter that is usual for surgical pins lies in the range about 1 millimeter (mm) to 2 mm, so it is possible with the broader faces 19 to lock surgical pins having a mean diameter in the range 1.6 mm to 2 mm, whereas the narrower faces 20 can be used for locking surgical pins having a mean diameter of about 1 mm to 1.6 mm.

Advantageously, for a pusher element 17 surmounted by the head 14, it is particularly useful to be able to split the pusher 12 so as to separate its head 14 from the pusher element 17. As is well known to the person skilled in the art, this can be achieved by providing a connection zone 25 between the head 14 and its junction with the pusher element 17 (FIG. 3) the connection zone being of smaller section and constituting an easily broken zone of weakness.

In use, once the surgeon has implanted the straight surgical pin 1 through two fractions of bone to be connected together, a protective plug 5 is engaged via the end 3 and the through channel 9.

The surgeon then positions the protective plug 5 at the desired location on the free length of the surgical pin 1 so that a length 3a of the surgical pin 1 projects therethrough. It is nevertheless possible, in the meaning of the invention, to position the protective plug 5 close to the end 3 of the surgical pin 1 so that no portion of the pin projects therethrough.

In either case, the surgeon then takes hold of locking means 12 of the invention by means of its head 14 and inserts the pusher element 17 into the locking orifice 11 after appropriately orienting the pusher element depending on the diameter of the pin 1 in question.

By pressing on the concave face 15, the surgeon forces the pusher element 17 until it locks the surgical pin 1 in the through channel 9 by the locking contact achieved with one of the faces 19 and 20 of the pusher element 17.

The surgeon can then separate the head 14 by breaking through the zone of weakness 25 (FIG. 3), the protective plug 5 then being locked in position on the surgical pin 1.

When a length 3a projects beyond the protective plug 5, the surgeon can firstly cut off the excess length 3a, if that should be necessary, and can also press on said surgical pin 1 so as to make a bend as shown in FIGS. 1 to 3, for example.

The entire disclosure if all applications, patents, and publications, cited above and below, and corresponding French Application No. 01-02577, filed Feb. 26, 2001 is hereby incorporated by reference.

From the foregoing description, one skilled in the art can easily ascertain the essential characteristics of this invention and, without departing from the spirit and scope of thereof, can make various changes and modifications of the invention to adapt it to various uses and conditions.

What is claimed is:

1. A surgical device for holding together and aligning at least two pieces of bone, the device comprising:
   a surgical pin suitable for being implanted axially in the pieces of bone to be held together; and
   a protective plug provided with a through channel for enabling it to be engaged on the pin, said plug including a locking orifice in which locking means can be inserted to lock the plug in position relative to the pin; wherein:
      the locking orifice opens out substantially tangentially into the through channel; and
      the locking means having a cross-section whereby upon being inserted into the locking orifice the locking means locks the plug relative to said pin positioned within said though channel by compressive/locking contact via the opening into the through channel.

2. A device according to claim 1, wherein the locking orifice is substantially orthogonal to the through channel.

3. A device according to claim 1, wherein the through channel opens out into a guide slot formed in the mass of the plug to enable a stop bend to be made in the pin.

4. A device according to claim 3, wherein said guide slot is U-shaped.

5. A device according to claim 1, wherein the locking means comprises a pusher element having a distal end which is to be inserted into said locking orifice and having a cross-section that increases going away from said distal end.

6. A device according to claim 5, wherein both the locking orifice and pusher element have cross-sections that are substantially in the form of a parallelogram.

7. A device according to claim 6, wherein both the locking orifice and the pusher element have substantially rectangular cross-sections.

8. A device according to claim 5, wherein the pusher element is surmounted by a head and is separable therefrom so that said head can be separated from the pusher element.

9. A device according to claim 8, wherein said head is concave.

10. A device according to claim 5, wherein the cross-section of the pusher element defines at least one first face and at least one second face wherein said first face is wider than said second face.

11. A device according to claim 10, wherein the surfaces of said faces are planar.

12. A device according to claim 11, wherein the pusher element has two wide first faces and two narrow second faces.

13. A device according to claim 10, wherein the surfaces of said faces are provided with portions in relief.

14. A device according to claim 13, wherein the surfaces of the faces are provided with catches.

15. A device according to claim 14, wherein the pusher element has two wide first faces and two narrow second faces.

16. A device according to claim 13, wherein the pusher element has two wide first faces and two narrow second faces.

17. A device according to claim 10, wherein the pusher element has two wide first faces and two narrow second faces.

* * * * *